United States Patent [19]

Fost et al.

[11] 4,084,055
[45] Apr. 11, 1978

[54] PREPARATION OF CHLORINATED INDAZOLES

[75] Inventors: Dennis Lynn Fost; Anthony David Wolf, both of Newark, Del.

[73] Assignee: E. I. Du Pont de Nemours and Company, Wilmington, Del.

[21] Appl. No.: 780,904

[22] Filed: Mar. 24, 1977

[51] Int. Cl.² ............................................ C07D 231/56
[52] U.S. Cl. .................................... 548/369; 71/92
[58] Field of Search ...................... 548/372; 548/369

[56] References Cited

FOREIGN PATENT DOCUMENTS 901,169   7/1962   United Kingdom.

Primary Examiner—Natalie Trousof
Assistant Examiner—Jane T. Fan

[57] ABSTRACT

This invention relates to a novel process for preparing indazoles by the reaction of phosgene with indazolones. The resulting indazoles are useful as herbicidal compounds.

17 Claims, No Drawings

PREPARATION OF CHLORINATED INDAZOLES

BACKGROUND OF THE INVENTION

This invention relates to a novel process for the production of 2-aryl-3-chloro-4,5,6,7-tetrahydro-2H-indazoles. In the past, 3-chloroindazoles were typically produced by reacting indazolones with phosphorus oxychloride.

British Pat. No. 901,169 describes the preparation of a compound of Formula I by reaction of phosgene with caprolactam.

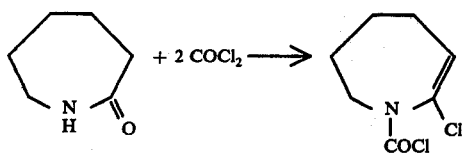
(I)

The preparation of imidoyl chlorides of Formula II is described in Chem. Ber., 95, 126 (1962).

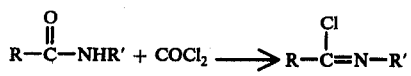
(II)

where
R is alkyl, aryl, or acetyl; and
R' is alkyl or aryl.

The use of phosphorus oxychloride to prepare 2-aryl-3-chloro-4,5,6,7-tetrahydro-2H-indazoles is disadvantageous because it produces undesired by-products (including inorganic phosphates) that contaminate the product and are difficult to remove. Moreover, the standard chlorinating reagents like $PCl_5$, $SOCl_2$, $SO_2Cl_2$ are ineffective in preparing 2-aryl-3-chloro-4,5,6,7-tetrahydro-2H-indazoles from 2-aryl-1,2,4,5,6,7-hexahydro-3H-indazol-3-ones. Since these indazoles are quite useful as herbicides, a process is needed which produces them in high yields. According to the instant invention such a process has been unexpectedly discovered.

DETAILED DESCRIPTION OF THE INVENTION

This invention relates to a novel process for preparing 2-aryl-3-chloro-4,5,6,7-tetrahydro-2H-indazoles of Formula V according to the following equation:

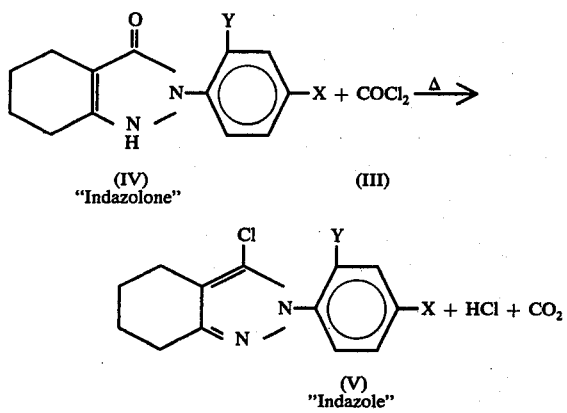

where
Y is hydrogen, fluorine or chlorine, preferably hydrogen or fluorine,
X is fluorine, chlorine, bromine, iodine, cyano, methoxy, or nitro, preferably fluorine, chlorine or bromine.

The process of this invention provides a high yield and convenient method for preparing compounds of Formula V. The reaction by-products — hydrogen chloride and carbon dioxide — are readily removed from the product.

The process is operated by contacting an indazolone of Formula IV with phosgene III, under reaction conditions, in a suitable reaction vessel.

Typical temperatures for the reaction would range between 100° and 250° C, although higher or lower temperatures may be utilized. Elevated temperature is preferred.

A solvent which does not react with phosgene nor interfere with the reaction may be used. Alternatively excess phosgene may serve both as a reactant and solvent.

The relative proportion of reactants and the reaction time may both be varied widely in the instant reaction. It is desirable to utilize a molar ratio of phosgene to indazolone (IV) of at least 1:1 in order to achieve a high conversion of indazolone to indazole. Alternatively, a molar ratio of phosgene to IV of less than 1:1 may be utilized, in which case, lower conversions would be obtained. In this latter case, the indazolone (IV) may readily be recycled if desired. Typical reaction times are between about 0.5 and 20 hours.

Pressure is not critical and may range from atmospheric to superatmospheric, typically from 1 to 50 atmospheres. Elevated pressure is preferred.

Any vessel which can withstand the corrosive action of phosgene and hydrochloric acid may be used for the process. An example would be a Hastalloy C-lined autoclave.

The preferred operating conditions for the instant process are as follows:
 a. Temperature: 100°–180° C
 b. Molar Ratio of Phosgene to Indazolone (IV): 0.1:1 to 20.0:1
 c. Molar Ratio of Solvent to Indazolone (IV): 1:1 to 50:1
 d. Pressure: 1 to 50 atmospheres
 e. Time: 1 to 20.0 hours Most preferred parameters for operation of the instant process are as follows:
 a. Temperature: 130°–160° C
 b. Molar Ratio of Phosgene to Indazolone (IV): 1.0:1 to 1.5:1
 c. Molar Ratio of Solvent to Indazolone (IV): 5:1 to 20:1
 d. Pressure: 10 to 30 atmospheres
 e. Time: 1 to 10 hours As indicated above, a solvent is optional. It may be preferred to use a solvent in order to improve mixing and contacting of the reactants, as influenced by chemical engineering choices of reaction equipment, temperature, pressure, ratio of reactants, and agitation. Preferred solvents boil between about 80° and 200° C. Examples of these solvents are non-polar aprotic solvents such as toluene, xylenes, chlorobenzene, benzene, or ortho-di-chlorobenzene. There is no intention to be bound to the use of the particular solvents named and one skilled in the art could readily determine which solvent may best be utilized given the other information supplied in the instant specification.

PREFERRED EMBODIMENT

In an embodiment of this process, a 2-aryl-1,2,4,5,6,7-hexahydro-3H-indazol-3one (IV) and a non-polar aprotic solvent (such as toluene, xylene, benzene, chlorobenzene, or o-dichlorobenzene), are charged to a Hastalloy C-lined autoclave. The autoclave is closed, evacuated to 0.025–0.10 atmosphere, and then phosgene is introduced from a pressurized cylinder. The autoclave is sealed and then heated at 130°–160° C with agitation. At the end of the reaction period (1 to 10 hours), the autoclave is cooled to ambient temperature and the excess phosgene, hydrochloric acid and carbon dioxide are vented through a caustic scrubber (containing aqueous sodium hydroxide solution). The autoclave is opened, the contents are discharged, and the product is isolated after removal of solvent by standard methods.

One skilled in the art will recognize that the exact combination of operating parameters interact in a complex fashion and may be chosen such that the reaction proceeds at a convenient rate without causing decomposition of either the starting material or product.

The indazoles of Formula V are useful as selective herbicides for control of weeds in crops such as rice and wheat.

In the following examples all parts are by weight and temperatures in ° C unless otherwise indicated:

EXAMPLE 1

Ten parts of 2-(4-chloro-2-fluorophenyl)-1,2,4,5,6,7-hexahydro-3H-indazol-3-one and 50 parts of chlorobenzene were charged to a Hastalloy C-lined shaker tube. The vessel was closed, charged with 10 parts of phosgene from a pressurized cylinder, and heated to 130° with constant shaking for 4 hours. The vessel was cooled to 25° C, vented, opened and discharged. The product mixture was evaporated under reduced pressure to give 10.1 parts of 2-(4-chloro-2-fluorophenyl)-3-chloro,4,5,6,7-tetrahydro-2H-indazole, m.p. 82°–85°. (90.7% pure as determined by gas chromatography).

EXAMPLE 2

Two hundred parts of 2-(4-chloro-2-fluorophenyl)-1,2,4,5,6,7-hexahydro-3H-indazol-3-one and 500 parts of toluene were charged to a Hastalloy C rockerbomb, filling it about ⅓ full. The vessel was closed, evacuated to 0.05 atmosphere, and then charged with 80 parts of phosgene from a pressurized cylinder. The sealed vessel was then heated at 150° and rocked for 5 hours. After cooling to 25°, the vessel was vented and discharged. The resulting solution was filtered to remove any insoluble impurities and evaporated under reduced pressure to give 213 parts of 2-(4-chloro-2-fluorophenyl)-3-chloro-4,5,6,7-tetrahydro-2H-indazole, m.p. 87°–90° (95.6% pure as determined by gas chromatography).

EXAMPLE 3

Fifty parts of 2-(4-chloro-2-fluorophenyl)-1,2,4,5,6,7-hexahydro-3H-indazol-3-one and 26 parts of mixed xylenes were charged to a 3-neck, round-bottomed flask fitted with a mechanical stirrer, dry ice condenser, an addition funnel with a gas inlet and dry ice condenser above it. The mixture was heated to 140° C with agitation under a nitrogen atmosphere. Phosgene was condensed into the addition funnel from a pressurized cylinder, and 20.9 parts of phosgene was added dropwise over several minutes. After 1 hour, the temperature of the reaction mixture was raised to 150° and held there for 2 hours. The solvent was then removed by vacuum distillation and the melted product was poured into a dish and allowed to cool. There was obtained 52.1 parts of 2-(4-chloro-2-fluorophenyl)-3-chloro-4,5,6,7-tetrahydro-2H-indazole, m.p. 72°–80° (70.3% pure as determined by gas chromatography).

EXAMPLE 4

One hundred parts of 2-(4-chloro-2-fluorophenyl)-1,2,4,5,6,7-hexahydro-3H-indazol-3-one was heated under a nitrogen atmosphere (nitrogen was slowly passed through the system at atmospheric pressure) in a 3-neck, round-bottomed flask, fitted with a mechanical stirrer, dry ice condenser, an addition funnel with a gas-inlet and dry ice condenser above it. Phosgene was condensed into the addition funnel from a pressurized cylinder, and 44 parts of phosgene was added dropwise over 2 hours, maintaining a temperature of 178°–180° in the reaction mixture for the first 1½ hours and allowing it to fall to 135° during the last ½ hour. The dry ice in the condenser was removed and the excess phosgene was passed through a 10% sodium hydroxide solution as it evaporated. The reaction mixture was poured out into a pan and allowed to cool. There was obtained 100.6 parts of 2-(4-chloro-2-fluorophenyl)-3-chloro-4,5,6,7-tetrahydro-2H-indazole, m.p. 81°–85° (80.4% pure as determined by gas chromatography).

What is claimed is:

1. A process for preparing

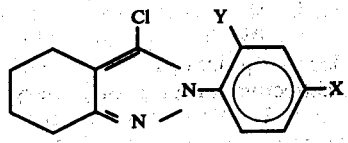

consisting essentially of contacting

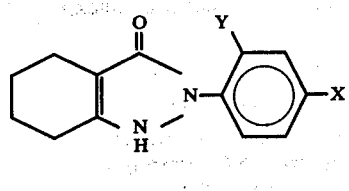

wherein
  Y is hydrogen, fluorine or chlorine; and
  X is fluorine, chlorine, bromine, iodine, cyano, methoxy or nitro,
with phosgene.

2. The process of claim 1 wherein the reaction takes place at elevated temperature.

3. The process of claim 1 wherein the reaction takes place in the presence of a solvent.

4. The process of claim 1 wherein the reaction takes place in the presence of a non-polar aprotic solvent having a boiling point between about 80° and 200° C.

5. The process of claim 1 wherein the ratio of phosgene to indazolone is at least 1:1.

6. The process of claim 1 wherein Y is hydrogen or fluorine and X is fluorine, chlorine or bromine.

7. The process of claim 1 wherein Y is hydrogen and X is chlorine.

8. The process of claim 1 wherein Y is fluorine and X is chlorine.

9. The process of claim 1 wherein Y is fluorine and X is bromine.

10. The process of claim 1 wherein the reaction takes place at elevated pressure.

11. A process for preparing

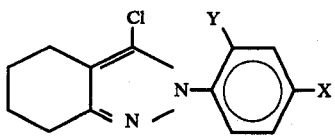

consisting essentially of contacting

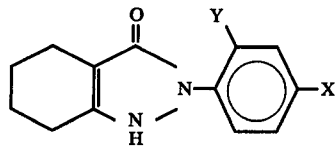

where
Y is hydrogen, fluorine or chlorine and
X is fluorine, chlorine, bromine, iodine, cyano, methoxy, or nitro,
with phosgene, at a temperature of about 130° to 160° C, in the presence of a non-polar, aprotic solvent having a boiling point between about 80° and 200° C, the molar ratio of phosgene to indazolone being between about 1.0:1 to 1.5:1, for a period of about one to 20 hours at an elevated pressure.

12. The process of claim 11 wherein Y is hydrogen or fluorine and X is fluorine, chlorine or bromine.

13. The process of claim 11 wherein Y is hydrogen and X is chlorine.

14. The process of claim 11 wherein Y is fluorine and X is chlorine.

15. The process of claim 11 wherein Y is fluorine and X is bromine.

16. The process of claim 11 wherein the pressure is between about 10 and 30 atmospheres.

17. The process of claim 11 wherein the reaction time is between about 1 and 10 hours.

* * * * *